United States Patent

Agouridas et al.

[11] Patent Number: 6,162,793
[45] Date of Patent: *Dec. 19, 2000

[54] ERYTHROMYCIN DERIVATIVES, METHOD FOR PREPARING SAME AND USE THEREOF AS DRUGS

[75] Inventors: Constantin Agouridas; Jean-Francois Chantot, both of Nogent-sur-Marne; Alexis Denis, Paris; Jean-Marie Pejac, Bondy, all of France

[73] Assignee: Hoechst Marion Roussel, France

[*] Notice: This patent is subject to a terminal disclaimer.

[21] Appl. No.: 09/230,126

[22] PCT Filed: Jul. 23, 1997

[86] PCT No.: PCT/FR97/01372

§ 371 Date: Feb. 11, 1999

§ 102(e) Date: Feb. 11, 1999

[87] PCT Pub. No.: WO98/03530

PCT Pub. Date: Jan. 29, 1998

[30] Foreign Application Priority Data

Jul. 24, 1996 [FR] France .................... 96 09285

[51] Int. Cl.⁷ .................... A61K 31/70; C07H 17/08; C07D 215/00
[52] U.S. Cl. .................... 514/29; 536/7.4; 546/152; 546/348
[58] Field of Search .................... 536/7.4; 514/29; 546/152, 348

[56] References Cited

U.S. PATENT DOCUMENTS

| | | | |
|---|---|---|---|
| 5,527,780 | 6/1996 | Agowidas et al. | 514/29 |
| 5,543,400 | 8/1996 | Agowidas et al. | 514/29 |
| 5,656,607 | 8/1997 | Agowidas et al. | 514/29 |
| 5,747,467 | 5/1998 | Agowidas et al. | 514/29 |

FOREIGN PATENT DOCUMENTS 0487411  5/1992  France .
0596802  5/1994  France .
0676409  10/1995  France .

*Primary Examiner*—Elli Peselev
*Attorney, Agent, or Firm*—Bierman, Muserlian and Lucas

[57] ABSTRACT

The compounds of formula (I):

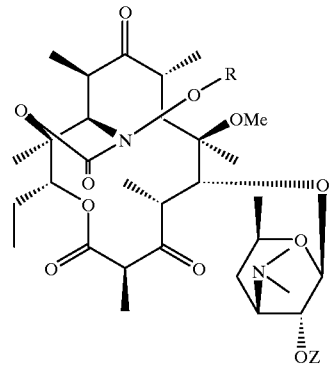

in which R is a hydrogen atom, an alkyl, optionally substituted by a halogen atom or a $(CH_2)_m Ar$ radical or a

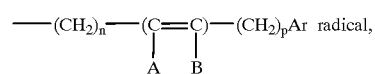

in which m represents an integer (1–8), n and p, identical or different, represent an integer (0–6), A and B, identical or different, represent a hydrogen or a halogen or an alkyl and Ar represents an aryl or heteroaryl, and Z represents a hydrogen or the remainder of a carboxylic acid, preparation process and use as medicaments.

13 Claims, No Drawings

ERYTHROMYCIN DERIVATIVES, METHOD FOR PREPARING SAME AND USE THEREOF AS DRUGS

This application is a 371 of PCT/FR97/01372 filed Jul. 23, 1997.

The present invention relates to new derivatives of erythromycin, their preparation process and their use as antibiotics.

A subject of the invention is the compounds of formula (I):

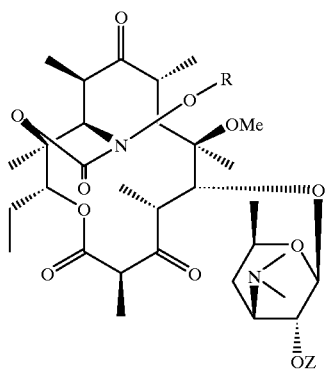

(I)

in which R represents a hydrogen atom, an alkyl containing up to 12 carbon atoms, optionally substituted by a halogen atom or a $(CH_2)_m Ar$ radical or a

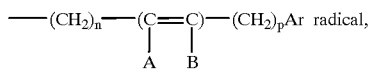

radical, in which m represents an integer comprised between 1 and 8, n and p, identical or different, represent an integer comprised between 0 and 6, A and B, identical or different, represent a hydrogen or a halogen atom or an alkyl radical containing up to 8 carbon atoms and Ar represents an aryl or heteroaryl radical, optionally substituted, and Z represents a hydrogen atom or the remainder of a carboxylic acid containing up to 18 carbon atoms.

In the definition of the substituents, the alkyl radical can be a methyl, ethyl, propyl, isopropyl, n-butyl, isobutyl or terbutyl, cyclobutyl, cyclopentyl, cyclohexyl, decyl or dodecyl radical. The halogen is preferably a fluorine, chlorine or bromine atom. The aryl radical can be a phenyl or naphthyl radical. The heteroaryl radical can be a thienyl, furyl, pyrolyl, thiazolyl, oxazolyl, imidazolyl, thiadiazolyl, pyrazolyl or isopyrazolyl radical, a pyridyl, pyrimidyl, pyridazinyl or pyrazinyl radical, or also an indolyl, benzofuranyl, benzothiazyl or quinolinyl radical. The aryl or heteroaryl radical can be substituted by one or more substituents chosen from the group constituted by hydroxyl radicals, halogen atoms, $NO_2$ radicals, $C\equiv N$ radicals, alkyl, alkenyl or alkynyl, O-alkyl, O-alkenyl or O-alkynyl, S-alkyl, S-alkenyl or S-alkynyl and N-alkyl, N-alkenyl or N-alkynyl radicals, containing up to 12 carbon atoms optionally substituted by one or more halogen atoms, the

radical, $R_a$ and $R_b$, identical or different, representing a hydrogen atom or an alkyl radical containing up to 12 carbon atoms, the

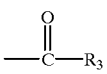

radical, $R_3$ representing an alkyl radical containing up to 12 carbon atoms, or an optionally substituted aryl or heteroaryl radical, carboxylic aryl, O-aryl or S-aryl radicals or heterocyclic aryl, O-aryl or S-aryl radicals with 5 or 6 members containing one or more heteroatoms, optionally substituted by one or more of the substituents mentioned below.

As the preferred heterocycle radical, the following radicals can be mentioned:

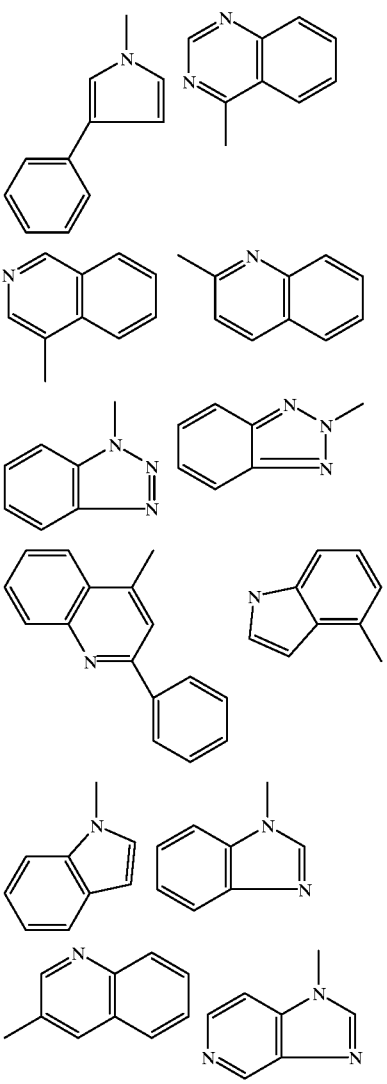

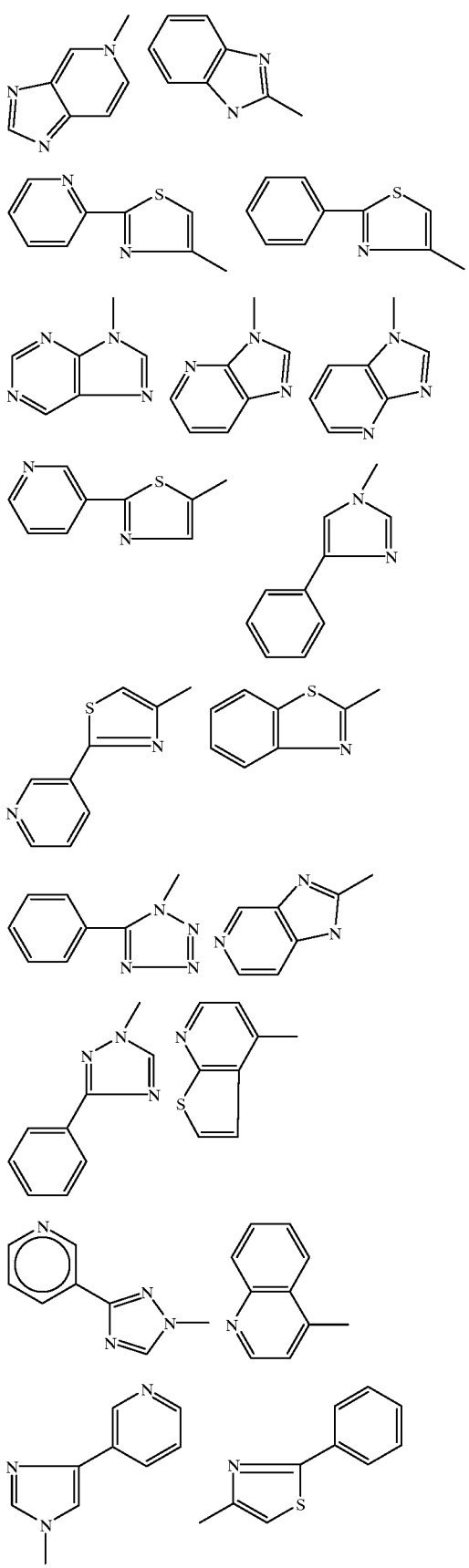
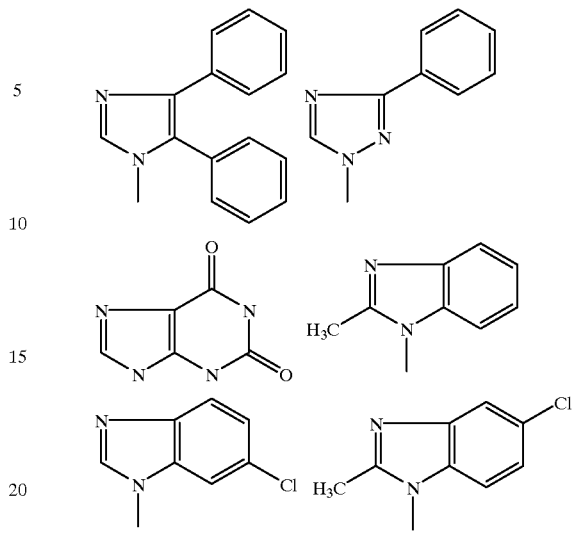

and the heterocyclic radicals envisaged in the European Patent Applications 487411, 596802, 676409 and 680967.

The radicals can be substituted by one or more of the substituents indicated above.

A more particular subject of the invention is the compounds of formula (I) in which Z represents a hydrogen atom, the compounds of formula (I) in which R represents a hydrogen atom, the compounds of formula (I) in which R represents $(CH_2)_m Ar$, m and Ar retaining the same meaning as previously, and in particular those in which R represents a $(CH_2)_{m'} Ar$ radical, in which m' represents the number 3, 4, 5 or 6, such as, for example, those in which Ar represents a 4-quinolinyl radical optionally substituted on one and/or the other of the 2 quinoline rings and quite especially those in which Ar represents a non-substituted 4-quinolinyl radical, or also the compounds of formula (I) in which Ar represents a radical:

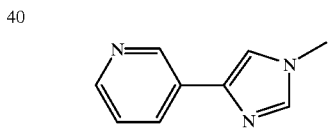

optionally substituted on one and/or the other of the 2 rings and quite especially those in which the Ar radical is not substituted.

A quite particular subject of the invention is the compounds whose preparation is given hereafter in the experimental part and in particular the compound of Example 4.

The products of general formula (I) have a very good antibiotic activity on gram ⊕ bacteria such as staphylococci, streptococci, pneumococci.

The compounds of the invention can therefore be used as medicaments in the treatment of infections caused by susceptible germs and in particular, in that of staphylococcia, such as staphylococcal septicemias, malignant staphylococcia of the face or skin, pyodermatitis, septic or suppurating wounds, boils, anthrax, phlegmons, erysipelas and acne, staphylococcia such as acute primary or post-influenzal angina, bronchopneumonia, pulmonary suppuration, streptococcia such as acute angina, otitis, sinusitis, scarlet fever, pneumococcia such as pneumonia, bronchitis; brucellosis, diphteri, gonococcal infection.

The products of the present invention are also active against infections caused by germs such as Haemophilus influenzae, Rickettsies, Mycoplasma pneumoniae, Chlamydia, Legionella, Ureaplasma, Toxoplasma or by germs of the Mycobacterium genus.

Therefore, a subject of the present invention is also, as medicaments and, in particular antibiotic medicaments, the products of formula (I) as defined above, as well as their addition salts with pharmaceutically acceptable mineral or organic acids.

A more particular subject of the invention is, as medicaments and, in particular antibiotic medicaments, the products of the examples.

A subject of the invention is also the pharmaceutical compositions containing at least one of the medicaments defined above as active ingredient.

These compositions can be administered by buccal, rectal, parenteral route or by local route as a topical application on the skin and mucous membranes, but the preferred administration route is the buccal route.

They can be solid or liquid and be presented in the pharmaceutical forms commonly used in human medicine, such as for example, plain or sugar-coated tablets, capsules, granules, suppositories, injectable preparations, ointments, creams, gels; they are prepared according to the usual methods. The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

These compositions can also be presented in the form of a powder intended to be dissolved extemporaneously in an appropriate vehicle, for example apyrogenic sterile water.

The dose administered is variable according to the illness treated, the patient in question, the administration route and the product considered. It can be, for example, comprised between 50 mg and 500 mg per day by oral route, for an adult for the product of Example 4.

The compounds of formula (II) used as starting products are described and claimed in the European Patent Application 0596802.

A subject of the invention is also a process characterized in that a compound of formula (II):

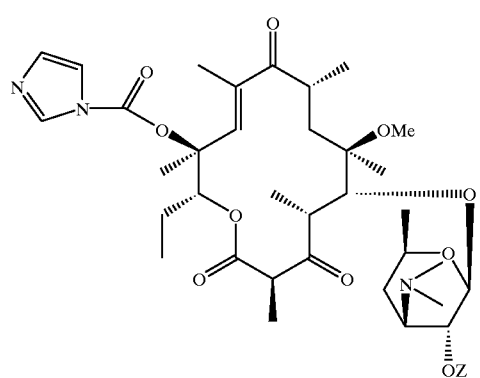

(II)

in which Z retains its previous meaning, is subjected to the action of hydroxylamine or a hydroxylamine hydrohalide, in order to obtain the compound of formula ($I_A$):

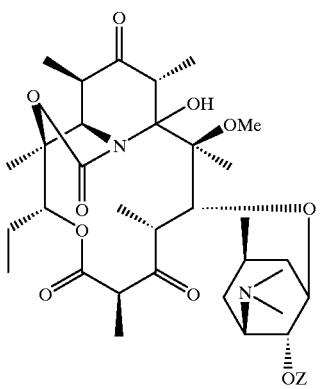

($I_A$)

which, if desired, is subjected to the action of a methanolysis agent in position 2', in order to obtain the corresponding compound of formula ($I_B$) in which Z represents a hydrogen atom

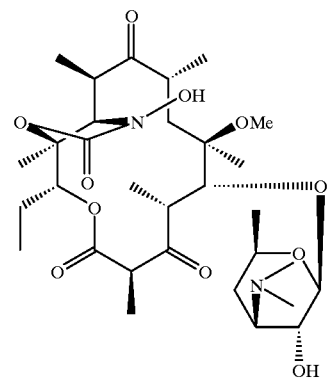

($I_B$)

then the compound ($I_A$) or ($I_B$) is subjected to the action of a compound of formula (III):

R'Hal    (III)

in which R' has the same meaning as R with the exception of the hydrogen and Hal represents a halogen atom, in order to obtain the corresponding compound of formula ($I_C$), which is optionally subjected to the action of a hydrogenation agent of the optional double bond of the

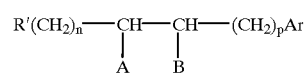

radical and/or to the action of an agent which releases the hydroxyl function in position 2'.

A subject of the invention is also the compounds of formula (III) whose preparation is given hereafter in the experimental part.

In a preferred implementation of the process of the invention:
the operation is carried out in the presence of an excess of hydroxylamine or hydroxylamine hydrohalide, in a solvent such as acetonitrile, dioxane, dimethylformamide, tetrahydrofuran, dimethoxyethane or dimethylsulphoxide,
the release of the hydroxyl in position 2' is carried out by methanolysis, the esterification in position 2' is carried out according to standard processes, Hal in the compound of formula (III) is preferably a bromine, chlorine or iodine atom, the reaction between compound (I$_A$) and compound (III) takes place in the presence of sodium hydride, the optional reduction of the chain

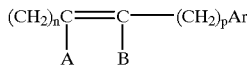

is carried out using hydrogen in the presence of a catalyst such as palladium, platinum and equally well in the presence or not of an acid such as hydrochloric acid or acetic acid.

The following examples illustrate the invention:

EXAMPLE 1

11,12-dideoxy-3-de((2,6-dideoxy-3-C-methyl-3-O-methyl-alpha-L-ribohexopyranosyl) oxy)-6-O-methyl-3-oxo-12,11-(oxycarbonyl (hydroxyimino))-erythromycin 200 cm$^3$ of acetonitrile and 20 g of 11-deoxy-10,11-didehydro-3-de((2,6-dideoxy-3-C-methyl-3-Omethyl-alpha-L-ribohexopyranosyl) oxy))-12-O-(11H-imidazol-1-yl) carbonyl)-6-O-methyl-3-oxo-erythromycin 2'-acetate is added to a solution containing 5.9 g of hydroxylamine hydrochloride and 20 cm$^3$ of water. Agitation is carried out for 3 hours, followed by evaporating to dryness, taking up in methanol and agitating again for 20 hours at ambient temperature. After evaporating to dryness, the residue is taken up in methylene chloride, washed with water, extracted with ethyl acetate, dried and evaporated to dryness. 17.4 g of product is obtained which is chromatographed on silica eluting with an AcOEt-TEA-MeOH mixture (98-0.75-0.75). 2.06 g of product is obtained by chromatography eluting with an isopropyl ether-TEA-MEOH system (90-5-5). The sought product is obtained.

NMR spectrum (400 Mhz in CDCl$_3$) ppm 0.88: CH$_3$CH$_2$; 1.2: 8 Me; 1.25: 5' Me; 1.31: 4 Me; 1.39: 2 Me; 1.33–1.49: 6 and 12 Me; 1.55 and 1.94: CH$_2$ in position 13; 1.67 and 1.89: CH$_2$ in position 7; 1.67: CH$_2$ in position 3'; 2.27: N(Me)$_2$; 2.46: H3'; 2.68: 6 OMe; 2.72: H8; 3.04: H4; 3.14: H10; 3.18: H2'; 3.57: H5'; 3.82: H11; 3.84: H2; 4.26: H5; 4.35: H1'; 5.14: H13.

EXAMPLE 2

(E) 11,12-dideoxy-3-de((2,6-dideoxy-3-C-methyl- 3-O-methyl-alpha-L-ribohexopyranosyl) oxy)-6-O-methyl-3-oxo-12,11-(oxycarbonyl (((3-phenyl 2-propenyl) oxy) imino))-erythromycin A solution containing 328 mg of the product of Example 1 and 4 cm$^3$ of DMF is cooled down to 0° C. 41 mg of sodium hydride at 60% in oil is added. Agitation is carried out for 15 minutes at 0° C. and 113 mg of cinnamyl bromide in solution in 2 ml of DMF on siliporite is added. The reaction medium is poured over ice, extracted with methylene chloride, washed with water, dried and evaporated to dryness. 420 mg of product is obtained which is purified on silica eluting with an isopropyl ether-triethylamine-methanol mixture (9-0.4-0.4). The sought product is obtained.

NMR spectrum (300 Mhz in CDCl$_3$) ppm 0.74: CH$_3$CH$_2$; 1.14: 8 and 10 Me; 1.24: 5' Me; 1.31: 4 Me; 1.41 and 1.49: 6 and 12 Me; 1.39: 2 Me; 1.50 and 1.82: CH$_2$ in position 14; 1.25 and 1.68: CH$_2$ in position 4'; 2.29: N(Me)$_2$; 2.48: H3'; 2.80: H8; 2.83: 6 Ome; 3.03: H10; 3.19: H2'; 3.54: H5'; 3.84: H2; 4.18: H11; 4.24: H5; 4.29: H1'; 4.52 and 4.61: OCH$_2$CH$_3$; 5.11: H13; 6.40 and 6.76: E ethylenics; 7.2 to 7.43: aromatics.

EXAMPLE 3

11,12-dideoxy-3-de((2,6-dideoxy-3-C-methyl-3-O-methyl-alpha-L-ribohexopyranosyl) oxy)-6-O-methyl-3-oxo-12,11-(oxycarbonyl((3-phenylpropoxy) imino))-erythromycin A mixture containing 57 mg of the product of Example 2, 15 ml of ethyl acetate and 8 mg of palladium on carbon is placed under a hydrogen atmosphere and agitation is carried out for 2 hours, followed by filtering, rinsing with ethyl acetate and evaporating to dryness. 56 mg of crude sought product is obtained which is purified on silica eluting with an isopropyl ether-triethylamine-methanol mixture (9-0.45-0.45). In this way 45 mg of sought product is obtained.

NMR spectrum (CDCl$_3$) ppm 0.89: CH$_3$CH$_2$; 1.13–1.15–1.24–1.29–1.36: CH$_3$—CH; 1.37–1.50: 6 and 12 Me; 1.99: Central CH$_2$; 2.27: N(Me)$_2$; 2.46: H3'; 2.69: 6 OMe; 2.74: CH$_2$Ph and H8; 2.97: H10; 3.08: H4; 3.17: H2'; 3.52: H5'; 3.82: H2; 3.90 and 3.98: CH$_2$O—N; 4.2: H5; 4.21: H11; 4.26: H1'; 5.12: H13; 7.1 to 7.3: Phenyl.

EXAMPLE 4

11,12-dideoxy-3-de((2,6-dideoxy-3-C-methyl-3-O-methyl-alpha-L-ribohexopyranosyl) oxy)-6-O-methyl-3-oxo-12,11-(oxycarbonyl (3-(4-quinolinyl) propoxy) imino)-erythromycin The operation is carried out as in Example 2, starting with the product of Example 1 and the product of Preparation 1, the sought product is obtained. M.p.=224° C.

NMR spectrum (CDCl$_3$) ppm 0.88: CH$_3$CH$_2$; 1.13: 8 Me; 1.18: 10 Me; 1.23: 5' Me; 1.29: 4 Me; 1.35: 2 Me; 1.34–1.51: 6 and 12 Me; 1.25 and 1.69: CH$_2$ in position 4'; 1.59 and 1.92: CH$_2$ in position 7; 2.13: Central CH$_2$ of the chain; 2.28: N(Me)$_2$; 2.45: H3'; 2.68: 6 OMe; 2.72: H8; 3.05: H10; 3.07: H4; 3.17: H2'; 3.28: CH$_2$C=; 3.52: H5'; 3.89: H2; 4.01 and 4.08: CH$_2$ONC=O; 4.16: H11; 4.2: H5; 4.27: H1'; 5.12: H13; 7.33–7.56–7.69–8.10–8.80: quinoline.

EXAMPLE 5

11,12-dideoxy-3-de((2,6-dideoxy-3-C-methyl-3-O-methyl-alpha-L-ribohexopyranosyl) oxy)-6-O-methyl-3-oxo-12,11-(oxycarbonyl (3-(4-(3-pyridinyl)-1H-imidazol-1-yl) propoxy) imino)-erythromycin The operation is carried out as in Example 2, starting with the product of Example 1 and the product of Preparation 2, the sought product is obtained.

NMR spectrum (CDCl$_3$) ppm 0.88: CH$_3$CH$_2$; 1.15: 10 Me; 1.17: 8 Me; 1.24: 5'Me; 1.29: 4 Me; 1.35: 2 Me; 1.37–1.51: 6 and 12 Me; 1.30–1.75: CH$_2$ in position 4'; 1.62–1.72: CH$_2$ in position 4'; 1.62–1.72: CH$_2$ in position 7; 1.60–1.92: CH$_2$ in position 14; 2.17: Central CH$_2$; 2.29: NMe$_2$; 2.48: H3'; 2.68: 6 O Me and H8; 3.06: H3; 3.08: H10; 3.19: H2'; 3.53: H5'; 2.83: H2; 3.98: CH$_2$—N; 4.05: H11; 4.21: H5; 4.27: H1'; 4.15 to 4.40: NO—CH$_2$; 5.09: H13; 7.49 and 7.68: imidazole; 7.29–8.1–8.46–8.90: pyridine.

Preparation 1: 4-(3-iodopropyl) quinoline

Stage A: ethyl 4-(3-chloropropyl)-2-(diethoxyphosphinyl)-1(2H)-quinolinecarboxylate A solution of 7.0 g of ethyl 2-(diethoxyphosphinyl) 1(2H)-quinolinecarboxylate and 70 ml of THF is cooled down to −65° C. 17.6 ml of butyllithium and 4 ml of bromochloro-propane are added over 15 minutes. Agitation is carried out for 3 hours 30 minutes, the reaction medium is poured into 50 cm$^3$ of ice-cooled water, followed by extraction with ethyl acetate, washing with water, drying and evaporating to dryness. The crude sought product is obtained which is purified by chromatography on silica eluting with a cyclohexane-ethyl acetate mixture (4-6), in this way 6.541 g of the sought product is obtained.

NMR spectrum (250 Mhz in CDCl$_3$) ppm 0.98–1.19–1.33: CH$_3$; 2.01: Central CH$_2$; 2.55 to 2.85:

=CH$_2$; 3.59: CH$_2$—CH$_2$—X; 3.71 to 4.14: CH$_2$ of POEt; 4.30: CH$_2$ of CO$_2$Et; 4.30: CH$_2$ of CO$_2$Et; 5.57: P—CH; 5.92: =CH—CH—P; 7.11–7.26–7.60: Aromatics.

Stage B: 4-(3-chloropropyl) quinoline 6.5 g of the product of Stage A, 65 cm$^3$ of ethyl alcohol and 65 cm$^3$ of 2N soda are agitated at 120° C. for 2 hours. After evaporating, extraction is carried out with ether, followed by washing with water, drying and evaporating to dryness. 1.87 g of product is obtained which is chromatographed on silica eluting with a methylene chloride-ethyl acetate mixture (8-2). 0.617 g of sought product is obtained.

NMR spectrum (CDCl$_3$) ppm 2.24: Central CH$_3$; 3.27: CH$_2$C=; 3.62: CH$_2$—X; 7.28–7.59–7.72–8.06–8.13–8.83: quinoline.

Stage C: 4-(3-iodopropyl) quinoline

A mixture of 268 mg of the product of Stage B, 5 ml of acetone, 1.042 g of sodium iodide and 30 mg of tetrabutylammonium iodide is agitated for 4 hours at 60° C. The acetone is evaporated off, the residue is taken up in methylene chloride, followed by washing with a 10% solution of sodium sulphite, drying and evaporating to dryness. 3.91 mg of sought product is obtained.

Preparation 2: 3-[1-(3-bromopropyl)-1H-imidazol-4-yl]-pyridine.

A solution containing 400 mg of 3-(1H-imidazol-4-yl) pyridine, 3 ml of DMF and 132 mg of sodium hydride at 60% in oil is agitated for 1 hour at 60° C. A solution of 3.22 g de dibromopropane in 2 ml of DMF is added dropwise. Agitation is carried out for 1 hour at ambient temperature, followed by pouring into ice-cooled water, extracting with ethyl acetate, drying and evaporating to dryness. The product obtained is chromatographed on silica eluting with a methylene chloride-methanol mixture (9-1). 306 mg of sought product is obtained.

Example of Pharmaceutical Composition

Compounds were prepared containing:
Product of Example 4 . . . 150 mg
Excipient s.q.f. . . . 1 g
Detail of excipient: starch, talc, magnesium stearate Pharmacological Study of the Products of the Invention Method of dilutions in liquid medium A series of tubes are prepared in which the same quantity of sterile nutritive medium is distributed. Increasing quantities of the product to be studied are distributed into each tube, then each tube is sown with a bacterial strain.

After incubation for twenty-four hours in a heating chamber at 37° C., the growth inhibition is evaluated by transillumination, which allows the minimal inhibitory concentrations (M.I.C.) to be determined, expressed in micrograms/cm$^3$.

The following results were obtained with the product of Example 4 (reading after 24 hours):

| GRAM$^+$ bacterial strains | |
|---|---|
| Staphylococcus aureus 011UC4 | 0.04 |
| Staphylococcus aureus 011G025I | 0.15 |
| Staphylococcus epidermidis 012GO11I | 0.15 |
| Streptococcus pyogenes group A 02A1UC1 | ≦0.02 |
| Streptococcus agalactiae group B 02B1HT1 | ≦0.02 |
| Streptococcus faecalis group D 02D2UC1 | ≦0.02 |
| Streptococcus faecium group D 02D3HT1 | ≦0.02 |
| Streptococcus sp | ≦0.02 |

| -continued | |
|---|---|
| GRAM$^+$ bacterial strains | |
| group G 02G0GR5 | |
| Streptococcus mitis 02mitCB1 | 0.04 |
| Streptococcus agalactiae group B 02B1SJ1 | 0.08 |
| Streptococcus pneumoniae 032UC1 | ≦0.02 |
| Streptococcus pneumoniae 030SJ5 | 0.04 |

In addition, the product of Example 4 has demonstrated a useful activity on the gram$^⊖$ bacterial strains: Haemophilus Influenzae 351HT3, 351CB12, 351CA1 and 351GR6.

What is claimed is:

1. A compound of the formula

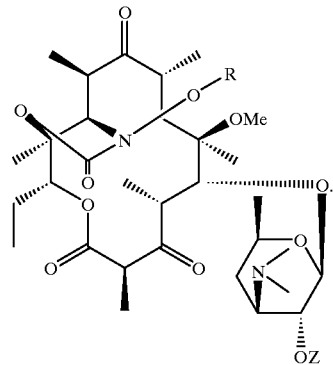

wherein R is selected from the group consisting of hydrogen, alkyl of 1 to 12 carbon atoms optionally substituted by halogen, —(CH$_2$)$_m$—Ar and

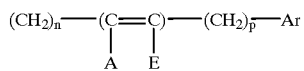

m is an integer from 1 to 8, n and p are individually an integer from 0 to 6, A and B are individually selected from the group consisting of hydrogen, halogen and alkyl of 1 to 8 carbon atoms, Ar is optionally substituted aryl or heteroaryl and Z is hydrogen or acyl of an organic carboxylic acid of up to 18 carbon atoms.

2. A compound of claim 1 wherein Z is hydrogen.
3. A compound of claim 1 wherein R is halogen.
4. A compound of claim 1 wherein R is —(CH$_2$)$_n$—Ar.
5. A compound of claim 4 wherein R is —(CH$_2$)$_n$—Ar and m' is an integer from 3 to 6.
6. A compound of claim 5 wherein Ar is 4-quinolinyl optionally substituted on at least one quinoline ring.
7. A compound of claim 5 wherein Ar is 4-quinolinyl.
8. A compound of claim 5 wherein Ar is

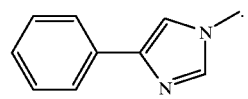

optionally substituted on at least one of the rings.

9. A compound of claim 8 wherein Ar is unsubstituted.
10. A compound of claim 1 which is 11,12-dideoxy-3-de (2,6-dideoxy-3-C-methyl-3-O-methyl alpha-L-ribohexopyranosyl) oxy)-6-O-methyl-3-oxo-12,11-(oxycarbonyl(3-(4-quinolinyl) propoxy) imino) erythromycin.

11. An antibacterial composition comprising an bactericidally effective amount of a compound of claim 1 and an inert pharmaceutical carrier.

12. A method of treating bacterial infections in warm-blooded animals comprising administering to warm-blooded animals a bactericidally effective amount of a compound of claim 1.

13. A compound selected from the group consisting of:

-4-(3-iodopropyl)-quinoline and

-3-[1-(3-bromopropyl)-1H-imidazo]-4-yl]-pyridine.

* * * * *

UNITED STATES PATENT AND TRADEMARK OFFICE
CERTIFICATE OF CORRECTION

PATENT NO.   : 6,162,793
DATED        : December 19, 2000
INVENTOR(S)  : Constantin Agouridas et al.

Page 1 of 1

It is certified that error appears in the above-identified patent and that said Letters Patent is hereby corrected as shown below:

Column 10,
Line 48, change "halogen" to -- hydrogen --.
Line 49, change "n" to -- m --.
Line 49, change "m" to -- m' --.
Line 60, change the structural formula to read as follows:

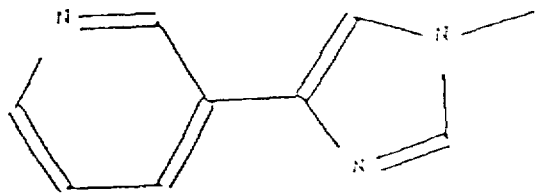

Signed and Sealed this

Sixth Day of November, 2001

Attest:

NICHOLAS P. GODICI
Attesting Officer    Acting Director of the United States Patent and Trademark Office